(12) United States Patent
Nakamura et al.

(10) Patent No.: US 9,233,371 B2
(45) Date of Patent: Jan. 12, 2016

(54) CONNECTION DEVICE AND ANALYZER

(75) Inventors: Yoichi Nakamura, Kobe (JP); Kohei Sugitani, Kobe (JP); Takaaki Nagai, Kobe (JP)

(73) Assignee: SYSMEX CORPORATION, Hyogo (JP)

( * ) Notice: Subject to any disclaimer, the term of this patent is extended or adjusted under 35 U.S.C. 154(b) by 0 days.

(21) Appl. No.: 12/838,179

(22) Filed: Jul. 16, 2010

(65) Prior Publication Data
US 2011/0014687 A1    Jan. 20, 2011

(30) Foreign Application Priority Data

Jul. 16, 2009   (JP) ................................. 2009-167718
Feb. 17, 2010   (JP) ................................. 2010-032668

(51) Int. Cl.
| | |
|---|---|
| *C12M 1/34* | (2006.01) |
| *F16L 39/04* | (2006.01) |
| *G01N 35/00* | (2006.01) |
| *B01L 3/00* | (2006.01) |
| *F16L 39/00* | (2006.01) |
| *G01N 35/10* | (2006.01) |

(52) U.S. Cl.
CPC ................. *B01L 3/523* (2013.01); *B01L 3/527* (2013.01); *B01L 3/561* (2013.01); *F16L 39/00* (2013.01); *G01N 35/1002* (2013.01); *B01L 2200/026* (2013.01); *B01L 2300/048* (2013.01)

(58) Field of Classification Search
None
See application file for complete search history.

(56) References Cited

U.S. PATENT DOCUMENTS

| | | | | |
|---|---|---|---|---|
| 4,444,358 A | * | 4/1984 | Spohn et al. | 239/284.1 |
| 5,022,547 A | * | 6/1991 | Spangler et al. | 220/23.4 |
| 2007/0122910 A1 | * | 5/2007 | Konrad et al. | 436/47 |
| 2011/0091364 A1 | * | 4/2011 | Voit | 422/547 |

FOREIGN PATENT DOCUMENTS

| | | | |
|---|---|---|---|
| EP | 2030684 A1 | * | 3/2009 |
| JP | 2004-163319 | * | 6/2004 |
| JP | 2004-163319 A | | 6/2004 |

* cited by examiner

*Primary Examiner* — P. Kathryn Wright
(74) *Attorney, Agent, or Firm* — Brinks Gilson & Lione

(57) ABSTRACT

A connection device for connecting to a plurality of fluid containers that have openings, and a sample analyzer body for analyzing samples using reagent, is disclosed, which comprises: a plurality of tubular members for passing liquid, the plurality of tubular members being inserted in the fluid containers through the openings of the plurality of fluid containers; a holding member to hold the plurality of tubular members; and a plurality of cover members to be fitted to the opening of the fluid container, wherein the plurality of cover members are arranged in a predetermined positional relationship on the holding member side of the plurality of tubular members; configured with a continuously decreasing cross sectional area toward the fluid container side; and the shape of the cross section of the cover member is substantially the same as the shape of the corresponding opening of the fluid container.

15 Claims, 15 Drawing Sheets

CONNECTION DEVICE AND ANALYZER

RELATED APPLICATIONS

This application claims priority under 35 U.S.C. §119 to Japanese Patent Application Nos. 2009-167718 filed on Jul. 16, 2009, and 2010-032668 filed on Feb. 17, 2010, the entire contents of which is hereby incorporated by reference.

BACKGROUND OF THE INVENTION

1. Technical Field of the Invention

The present invention relates to a connection device and analyzer, and specifically relates to a connection device and analyzer configured for inserting a plurality of tubular members into a plurality of fluid containers.

2. Description of the Related Art

It is known that conventional connection devices and analyzers are configured to insert a plurality of tubular members in a plurality of fluid containers (for example, refer to Japanese Laid-Open Patent Publication No. 2004-163319).

Japanese Laid-Open Patent Publication No. 2004-163319 discloses a blood analyzer comprising: a connection mechanism comprising a plurality of tubular members to be inserted into a plurality of containers accommodating reagent or waste fluid, a plurality of holding members to hold the respective plurality of tubular members, one support member to support the plurality of holding members, and a vertical movement mechanism for individually inserting the plurality of tubular members into each corresponding fluid container; and a blood analyzer body.

In the blood analyzer disclosed in Japanese Laid-Open Patent Publication No. 2004-163319, the opening of the fluid container is formed on an upwardly protruding open part, and the opening is blocked by the holding member covering the open part.

In a structure in which a holding member covers an open part, the opening cannot be blocked by the holding member if the holding member is not accurately positioned relative to the opening as in the case of the blood analyzer disclosed in Japanese Laid-Open Patent Publication No. 2004-163319. A precisely designed vertical movement mechanism is therefore required.

SUMMARY OF THE INVENTION

The scope of the present invention is defined solely by the appended claims, and is not affected to any degree by the statements within this summary.

A first connection device for connecting to a plurality of fluid containers that have openings, and a sample analyzer body for analyzing samples using reagent, embodying features of the present invention includes: a plurality of tubular members for passing liquid, the plurality of tubular members being inserted in the fluid containers through the openings of the plurality of fluid containers; a holding member to hold the plurality of tubular members; and a plurality of cover members to be fitted to the opening of the fluid container, wherein the plurality of cover members are arranged in a predetermined positional relationship on the holding member side of the plurality of tubular members; configured with a continuously decreasing cross sectional area toward the fluid container side; and the shape of the cross section of the cover member is substantially the same as the shape of the corresponding opening of the fluid container.

A first analyzer embodying features of the present invention includes: he connection device of claim 1; and an analyzer body configured to analyze samples using reagent, wherein the analyzer body is connected to a plurality of reagent containers by the connection device.

A second analyzer embodying features of the present invention includes: an analyzer body for analyzing samples; and a connection device for connecting the analyzer body and a plurality of fluid container without openings, wherein the connection device comprises: a plurality of tubular members for passing liquid, the plurality of tubular members being inserted in the fluid containers through the openings of the plurality of fluid containers; a holding member to hold the plurality of tubular members; and a plurality of cover members to be fitted to the opening of the fluid container, wherein the plurality of cover members are arranged in a predetermined positional relationship on the holding member side of the plurality of tubular members; configured with a continuously decreasing cross sectional area toward the fluid container side; and the shape of the cross section of the cover member is substantially the same as the shape of the corresponding opening of the fluid container.

A third analyzer embodying features of the present invention includes: an analyzer body for analyzing samples using reagent; a plurality of reagent containers with openings; and a connection device for connecting the analyzer body and the plurality of reagent containers, wherein the connection device comprises: a plurality of tubular members for passing reagent, the plurality of tubular members being inserted in the reagent containers through the openings of the plurality of reagent containers; a holding member to hold the plurality of tubular members; and a plurality of cover members to be fitted to the openings of the reagent containers, wherein the plurality of cover members are arranged in a predetermined positional relationship on the holding member side of the plurality of tubular members; configured with a continuously decreasing cross sectional area toward the reagent container side; and the shape of the cross section of the cover member is substantially the same as the shape of the corresponding opening of the reagent container.

DETAILED DESCRIPTION OF THE PREFERRED EMBODIMENTS

The embodiments of the present invention are described hereinafter based on the drawings.
(First Embodiment)

The overall structure of the analyzing apparatus 100 of the first embodiment of the present invention is described below with reference to FIGS. 1 through 8.

Figure 1:
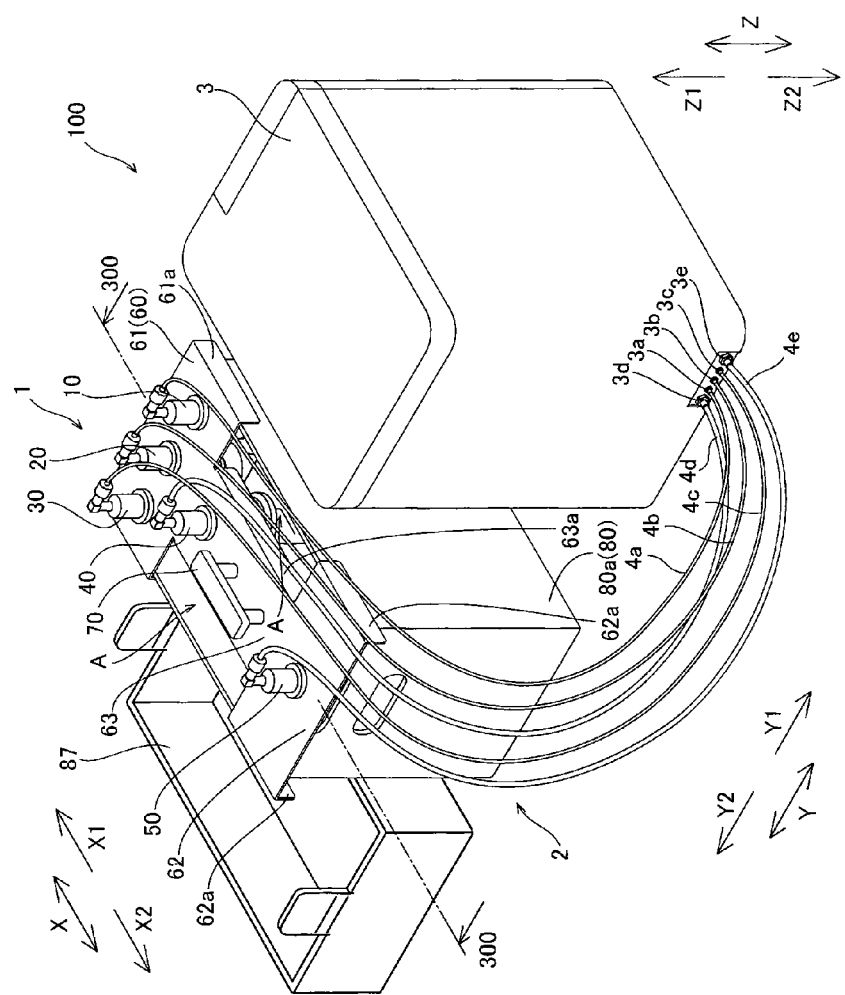
FIG. 1 is a perspective view showing the structure of the connection device, reagent set, and sample analyzer of a first embodiment of the present invention.

As shown in FIG. 1, the analyzing apparatus 100 of the first embodiment is configured by a connection device 1, reagent set 2 arranged so as to cover the connection device 1 from above (side in the arrow Z2 direction), and sample analyzer 3 (blood cell counting apparatus for counting blood cells in blood in the first embodiment) for analyzing blood (samples) of an animal.

Figure 2:
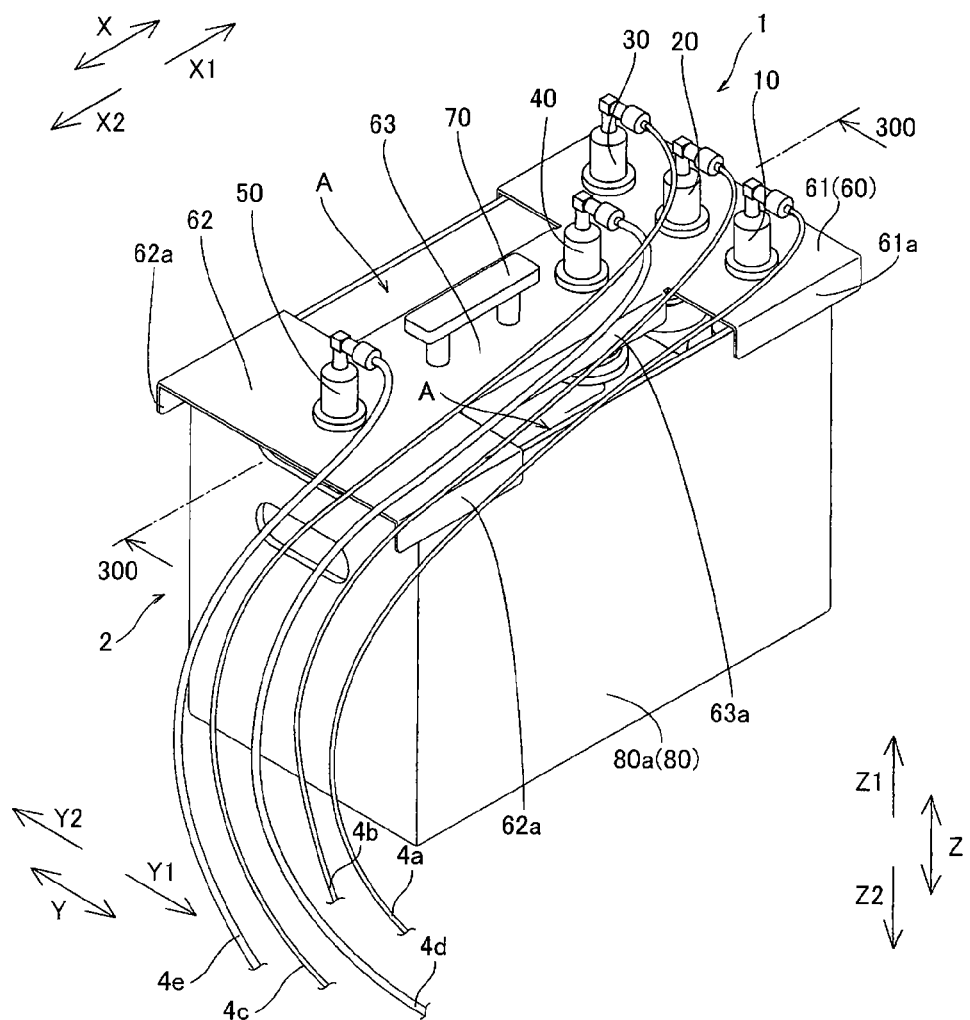
FIG. 2 is a perspective view showing the connection device arranged in the reagent set in the first embodiment of the present invention.
Figure 3:
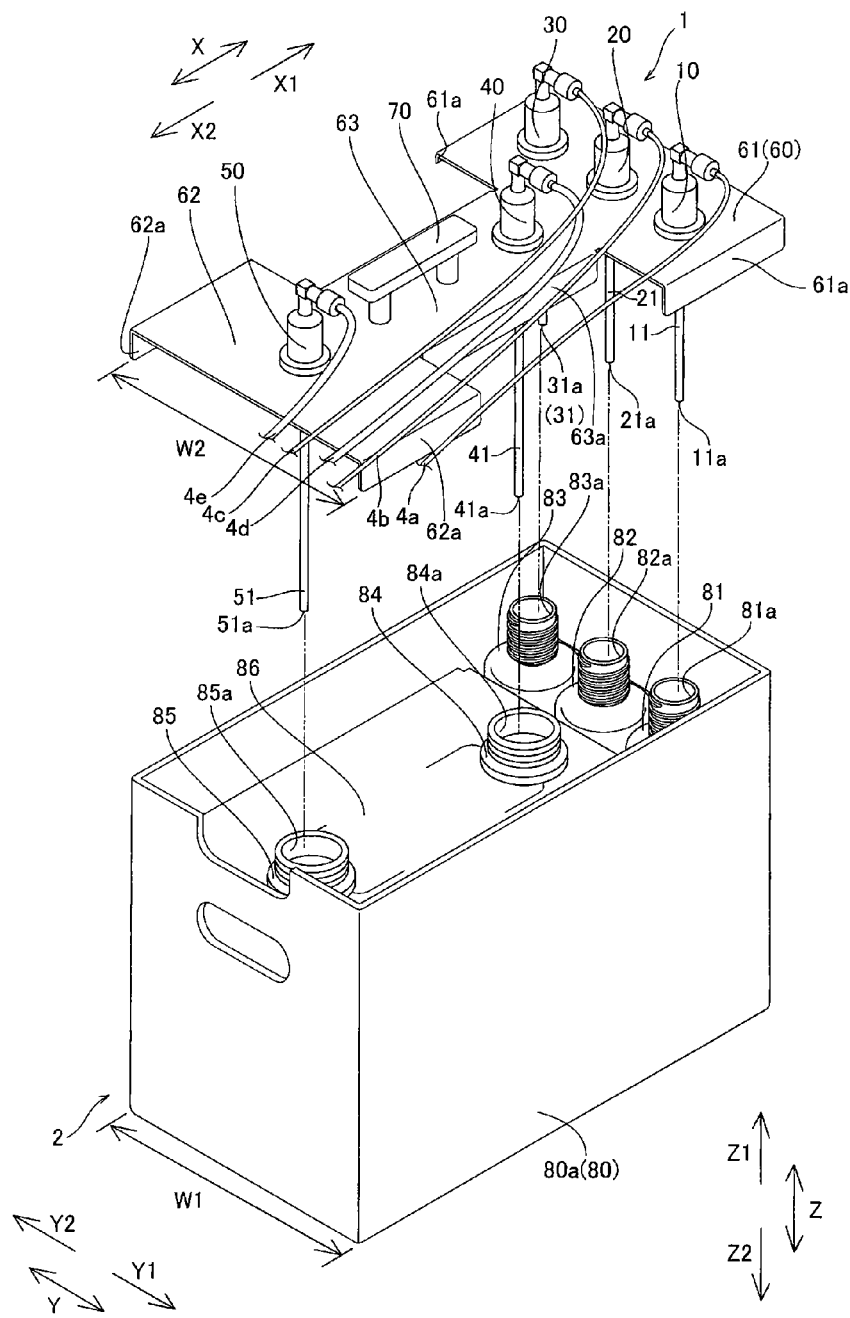
FIG. 3 is a perspective view showing the connection device removed from the reagent set in the first embodiment of the present invention.

As shown in FIGS. 1 through 3, the connection device 1 includes, on the side in the arrow X1 direction, reagent extraction units 10, 20, and 30 disposed in a row in the Y direction, reagent extraction unit 40 disposed near the center in the X direction, and waste fluid discharge unit 50 disposed on the side in the arrow X2 direction. The reagent extraction units 10, 20, 30, 40, and waste fluid discharge unit 50 are anchored and held by a metal holding member 60. A handle 70 is provided substantially in the center in the X direction of the holding member 60 for positioning the connection device 1 in the reagent set 2 while held by a user. The handle 70 is extends in the X direction.

As shown in FIG. 1, the reagent extraction units 10, 20, 30, 40, and waste fluid discharge unit 50 are connected to the aspiration openings 3a, 3b, 3c, 3d, and 3e of the sample analyzer 3 through tubes 4a, 4b, 4c, 4d, and 4e, respectively.

As shown in FIG. 3, in the reagent set 2, a hemolytic agent storage container 81, hemolytic agent storage container 82, staining agent storage container 83, diluting liquid container 84, and waste fluid container 85 are arranged inside a substantially rectangular box 80 having a width W1 in the Y direction. The hemolytic agent storage container 81 accommodates reagent (hemolytic agent) for measuring hemoglobin, and hemolytic agent storage container 82 accommodates reagent (hemolytic agent) for white blood cell classification and measurement. The staining agent storage container 83 accommodates reagent (diluting liquid) for measuring reticulocytes, and the diluting liquid container 84 accommodates reagent (diluting liquid). The waste fluid container 85 is configured to collect the reagent and sample used in the sample analyzer 3 as waste fluid.

An anchor member 86 is arranged inside the box 80 to dispose the hemolytic agent storage container 81, hemolytic agent storage container 82, staining agent storage container 83, diluting liquid container 84, and waste fluid container 85 at predetermined positions. As shown in FIG. 1, the reagent set 2 includes a cover 87 that is mountable so as to cover the box 80 before and after use of the reagent set 2.

As shown in FIG. 3, the hemolytic agent storage container 81, hemolytic agent storage container 82, and staining agent storage container 83 are arranged in a row in the lateral direction (Y direction) on the side in the arrow X1 direction of the box 80. The diluting liquid container 84 is disposed substantially in the center in the X direction of the box 80 so as to correspond to the reagent extraction unit 40, and the waste fluid container 85 is disposed on the side in the arrow X2 direction of the box 80 so as to correspond to the waste fluid discharge unit 50. The diluting liquid container 84 and waste fluid container 85 are further disposed side by side in the longitudinal direction (X direction).

The hemolytic agent storage container 81 is disposed on the side in the arrow Y1 direction of the box 80 so as to correspond to the reagent extraction unit 10, and the hemolytic agent storage container 82 is disposed near the center in the Y direction of the box 80 so as to correspond to the reagent extraction unit 20. The staining agent storage container 83 is also disposed on the side in the arrow Y2 direction of the box 80 so as to correspond to the reagent extraction unit 30. The hemolytic agent storage container 81, hemolytic agent storage container 82, and staining agent storage container 83 are containers with substantially similar shape, and the opening 81a of the hemolytic agent storage container 81, opening 82a of the hemolytic agent storage container 82, and opening 83a of the staining agent storage container 83 have an inner side surface with an internal diameter D1 (refer to FIG. 4) in a planar view.

The diluting liquid container 84 and waste fluid container 85 are containers with substantially similar shape, and the opening 84a of the diluting liquid container 84 and opening 85a of the waste fluid container 85 have an inner side surface with an internal diameter D2 (refer to FIG. 4) in a planar view. The openings 84a and 85a are movable in a certain range in a horizontal direction because the diluting liquid container 84 and waste fluid container 85 are configured by a material that allows the shape to be deformable according to the liquid accommodated therein.

As shown in FIG. 3, the reagent extraction units 10, 20, 30, and 40 are provided with long and narrow reagent extracting tubes 11, 21, 31, 41, respectively, for passing the reagent accommodated within the units. The reagent extracting tubes 11, 21, 31, and 41 are configured to be inserted in the corresponding opening 81a of the hemolytic agent storage container 81, opening 82a of the hemolytic agent storage container 82, opening 83a of the staining agent storage container 83, and opening 84a of the diluting liquid container 84, respectively. The waste fluid discharge unit 50 is provided with a long and narrow waste fluid discharging tube 51 for passing waste fluid accommodated within the unit. The waste fluid discharging tube 51 is configured to be inserted in the corresponding opening 85a of the waste fluid container 85 accommodating the waste fluid. Note that the reagent extracting tubes 11, 21, 31, 41, and waste fluid discharging tube 51 have the same internal diameter.

Figure 4:
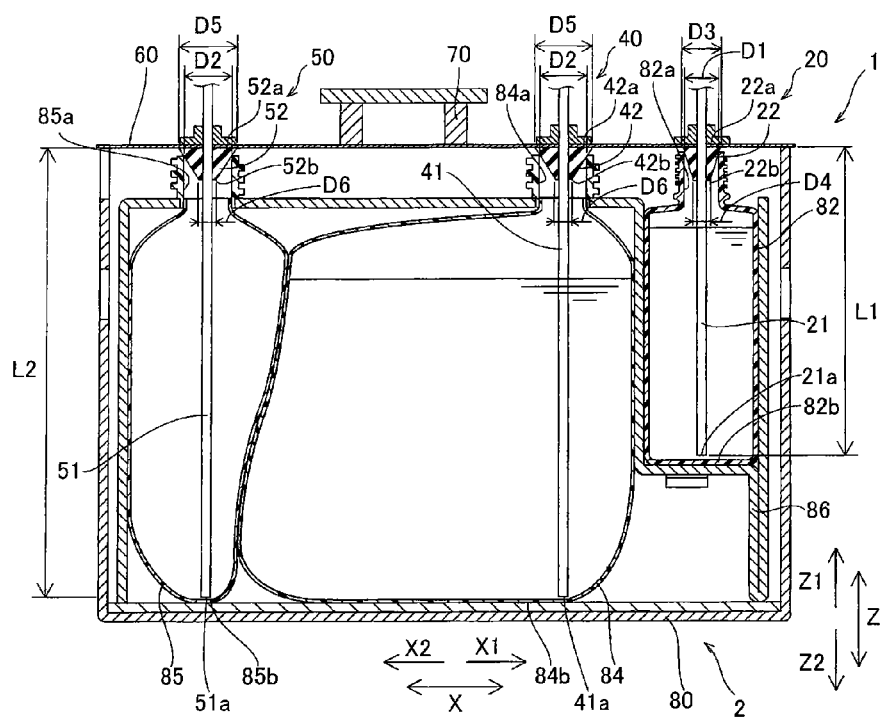
FIG. 4 is a cross sectional view along the 300-300 line of FIG. 2 showing the connection device arranged in the reagent set in the first embodiment of the present invention.

As shown in FIG. 4, the reagent passes through the inside of the reagent extracting tubes 11, 21, 31, and 41 toward the side in the arrow Z1 direction by aspirating reagent from the tips 11a, 21a, 31a, 41a on the side in the arrow Z2 direction of the reagent extracting tubes 11, 21, 31, and 41. The waste fluid passing toward the side in the arrow Z2 direction from inside the waste fluid discharging tube 51 is discharged from the tip 51a on the side in the arrow Z2 direction of the waste fluid discharging tube 51. Note that the reagent extracting tubes 11, 21, 31, 41, and waste fluid discharging tube 51 extend substantially linearly in the Z direction from the holding member 60 to the tips 11a, 21a, 31a, 41a, and 51a, respectively.

The reagent extracting tubes 11, 21, and 31, are configured so that the length from the holding member 60 to the tips 11a, 21a, 31a is substantially the same length L1. The reagent extracting tube 41 and waste fluid discharging tube 51 are configured so that the length from the holding member 60 to the tips 41a and 51a is substantially the same length L2. Note that the length L2 is longer than the length L1.

As shown in FIG. 4, the tips 11a, 21a, and 31a are positioned near the base (not shown in the drawing) of the hemolytic agent storage container 81, near the base 82b of the hemolytic agent storage container 82, and near the base (not shown in the drawing) of the staining agent storage container 83, respectively, when the connection device 1 is arranged in the reagent set 2. Similarly, the tips 41a and 51a are positioned near the base 84b of the diluting liquid container 84 and near the base 85b of the waste fluid container 85, respectively, when the connection device 1 is arranged in the reagent set 2.

Figure 5:
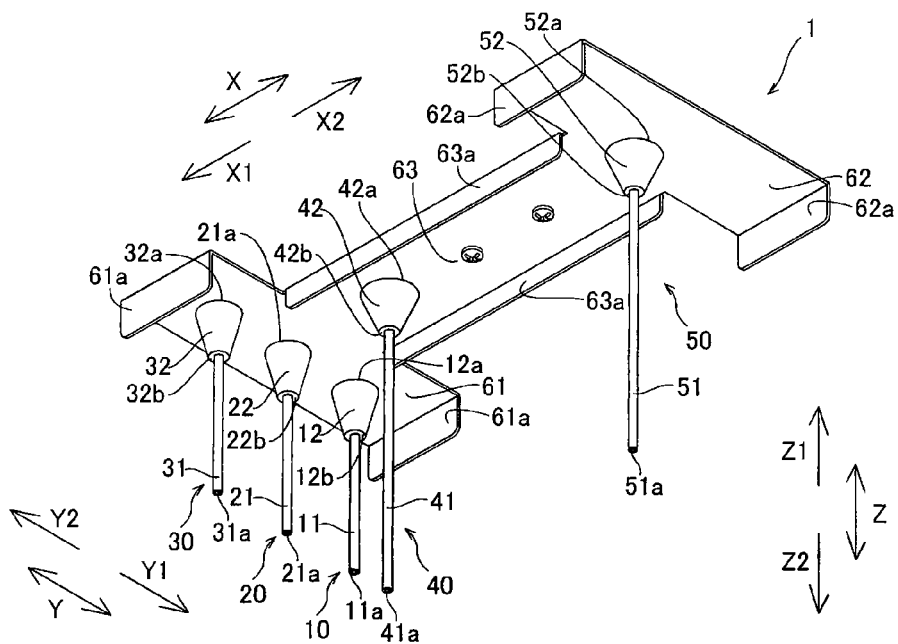
FIG. 5 is a perspective view from below the connection device in the first embodiment of the present invention.
Figure 6:
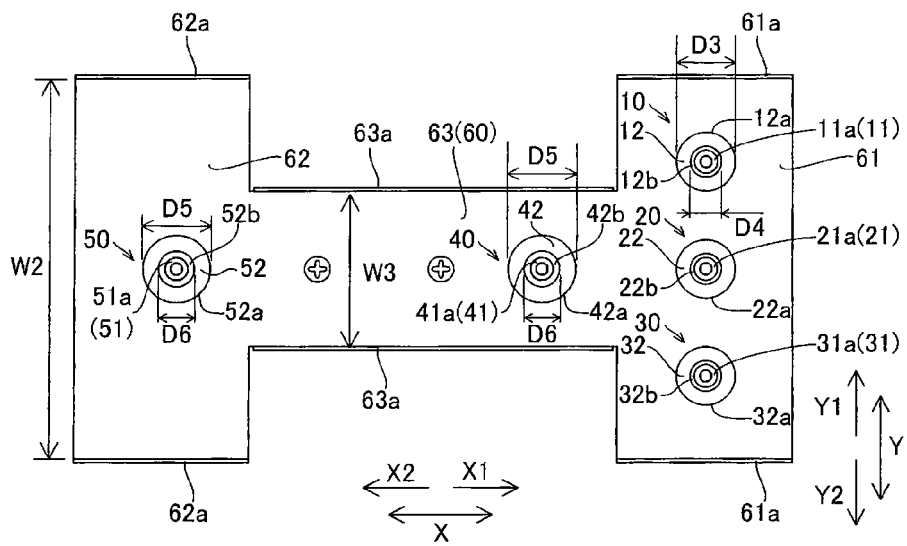
FIG. 6 is a plan view showing the back surface of the connection device in the first embodiment of the present invention.

As shown in FIGS. 4 through 6, the reagent extraction units 10, 20, and 30 are provided with cover members 12, 22, and 32, respectively. The cover members 12, 22, and 32 are arranged on the holding member 60 side (side in the arrow Z1 direction) of the reagent extraction units 11, 21, and 31, and are disposed so as to be in contact with the back surface (surface on the side in the arrow Z2 direction) of the holding member 60. The reagent extraction unit 40 and waste fluid discharge unit 50 are provided with cover member 42 and 52, respectively. The cover members 42 and 52 are arranged on the holding member 60 side (side in the arrow Z1 direction) of the reagent extracting tube 41 and waste fluid discharging tube 51, and are disposed so as to be in contact with the back surface of the holding member 60.

The cover members 12, 22, 32, 42, and 52 are fixedly attached to the holding member 60 and the respective reagent extracting tube 11, 21, 31, 41, and waste fluid discharging tube 51. Note that the cover members 12, 22, 32, 42, and 52 are formed of silicone rubber, which is resistant to chemicals.

In the first embodiment, the cover members 12, 22, 32, 42, and 52 have an inverted circular cone shape, as shown in FIGS. 4 and 5. That is, as shown in FIG. 4, the cover members 12, 22, 32, 42, and 52 have a circular cross sectional shape in cross section (plane formed by the X direction and Y direction), wherein the cross sectional area (surface area in the plane formed in the X direction and Y direction) continuously decreases from the side in the arrow Z1 direction toward the side in the arrow Z2 direction.

In the first embodiment, the top surface 12a, 22a, 32a of the cover members 12, 22, 32 has an outer diameter D3, respectively, whereas the bottom surface 12b, 22b, 32b has an outer diameter D4, respectively, that is smaller than the diameter D3. In this case, the outer diameter D3 is also larger than the inner diameter D1 of the opening 82a of the hemolytic agent storage container 82, and opening 83a of the hemolytic agent storage container 83. Thus, the surface area of the top surfaces 12a, 22a, and 32a is greater than the surfaces area of the openings 81a, 82a, 83a. However, the outer diameter D4 is smaller than the inner diameter D1 of the openings 81a, 82a, and 83a. In this way, the cross section of the cover members 12, 22, and 32, at the height position of the top end of the openings 81a, 82a, 83a in which they are installed, have a surface area identical to the surface area of the opening 81a, surface area of the opening 82a, and surface area of the opening 83a.

The top surfaces 42a and 52a of the cover members 42 and 52 have an outer diameter D5, whereas the bottom surfaces 42b and 52b have an outer diameter D6 that is smaller than the outer diameter D5. In this case, the outer diameter D5 is greater than the inner diameter D2 of the opening 84a of the diluting liquid container 84 and the opening 85a of the waste fluid container 85. Therefore, the surface area of the top surfaces 42a and 52a is greater than the surface area of the openings 84a and 85a. However, the outer diameter D6 is smaller than the inner diameter D2 of the openings 84a and 85a. Therefore, the cross section of the cover members 42 and 52, at the height position of the top end of the openings 84a and 85a in which they are installed, have a surface area identical to the surface area of the opening 84a and the surface area of the opening 85a. Note that the outer diameter D3 is smaller than the outer diameter D5.

As shown in FIG. 4, when the cover members 12, 22, 32, 42, and 52 are installed in openings 81a, 82a, 83a, 84a, and 85a, respectively, the cross sectional surface area is within a horizontal plane. Thus, when the connection device 1 is installed, it is possible to prevent inclination of the reagent extracting tubes 11, 21, 31, 41, and waste fluid discharging tube 51 fixedly attached to the holding member 60 through the cover members 12, 22, 32, 42, and 52, respectively.

Figure 7:
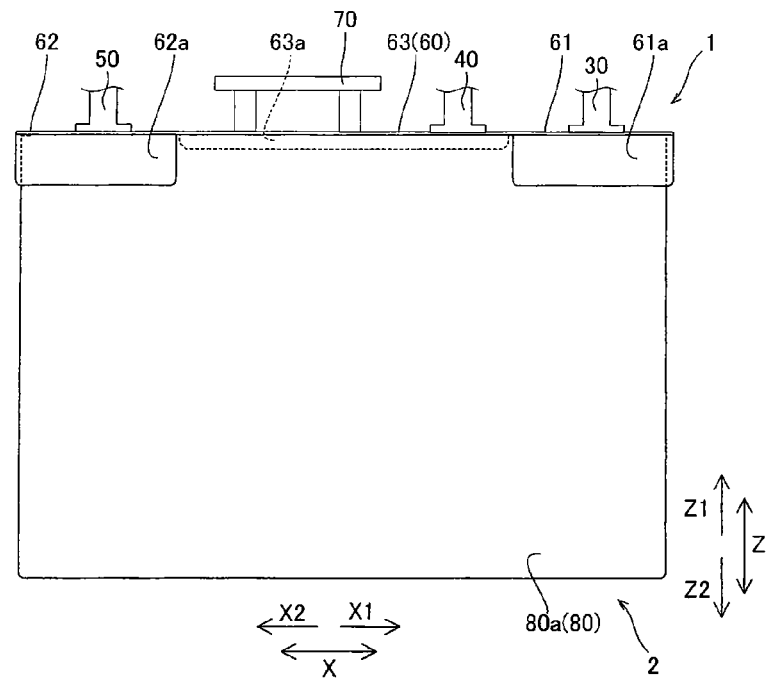
FIG. 7 is a side view from the arrow Y1 side showing the connection device arranged in the reagent set in the first embodiment of the present invention.

As shown in FIG. 6, the holding member 60 has the shape of the letter H in a planar view. As shown in FIGS. 6 and 7, the holding member 60 includes a latching part 61 capable of locking to the box 80 (refer to FIG. 7) and disposed on the side in the arrow X1 direction, latching part 62 capable of locking to the box 80 and disposed on the side in the arrow X2 direction, and latch release 63 for connecting the latching parts 61 and 62 and disposed substantially in the center in the X direction. The latching part 61 is configured to anchor and hold the reagent extraction units 10, 20, and 30. Similarly, the latching part 62 is configured to anchor and hold the waste fluid container 50, and the latch release 63 is configured to anchor and hold the reagent extraction unit 40 and handle 70 (refer to FIG. 7).

Figure 8:
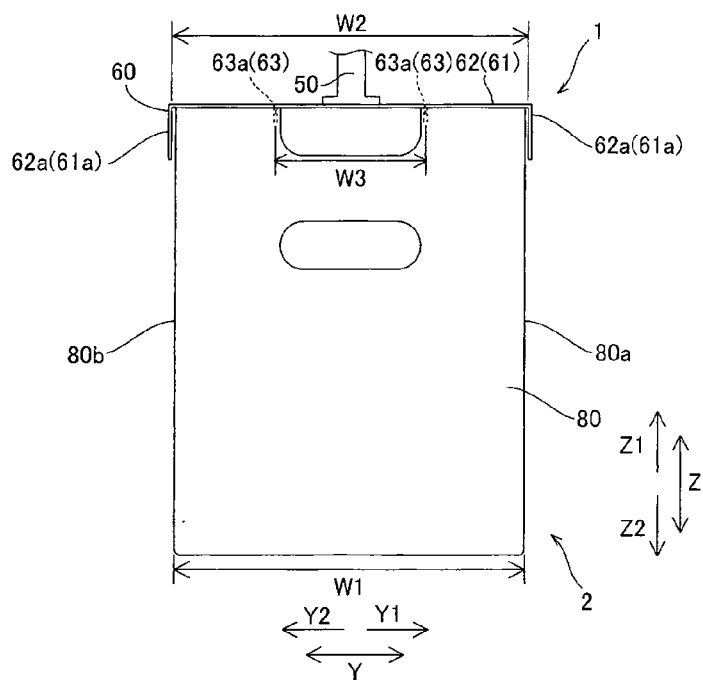
FIG. 8 is a side view from the arrow X2 side showing the connection device arranged in the reagent set in the first embodiment of the present invention.

As shown in FIG. 8, the latching parts 61 and 62 have a width W2 in the Y direction, whereas the latch release 63 has a width W3 in the Y direction. The width W2 of the latching parts 61 and 62 is slightly larger than the width W1 in the Y direction of the box 80. In this way, the latching parts 61 and 62 can be mounted on the top end surface of the bilateral surfaces (side surfaces 80a and 80b) in the Y direction of the box 80. However, the width W3 of the latch release 63 is smaller than the width W1 of the box 80. In this way, exposed part A (refer to FIG. 2), which allows verification of the interior of the box 80, is provided on both sides in the Y direction of the latch release 63.

Side surfaces 61 a, 62a, and 63a, which are folded toward the arrow Z2 direction, are provided on bilateral ends in the Y direction of the latching parts 61 and 62, and latch release 63. The side surfaces 61a, 62a, and 63a have the function of improving the mechanical strength of the holding member 60.

The side surfaces 61 a and 62a are provided along the bilateral side surfaces (side surfaces 80a and 80b) in the Y direction of the box 80, as shown in FIGS. 7 and 8. In this way, when the holding member 60 is arranged in the box 80 and moved in the Y direction, the movement of the holding member 60 in the Y direction (lateral direction) is regulated by the side surfaces 61a and 62a because the side surfaces 61a and 62a are in contact with (latched) the side surfaces 80a and 80b.

The arrangement and operation of the connection device 1 in the reagent set 2 of the first embodiment of the present invention is described below with reference to FIGS. 2 through 4, and 9 through 11.

A user first removes the cover 87 mounted on the box 80, and removes the caps (not shown in the drawings) screwed on the respective hemolytic agent storage container 81, hemolytic agent storage container 82, staining agent storage container 83, diluting agent container 84, and waste fluid container 85.

As shown in FIG. 3, the user prepares the connection device 1, which is connected to the sample analyzer 3 (refer to FIG. 1) through the tubed 4a, 4b, 4c, 4d, and 4e. Thereafter, while gripping the handle 70 so that the holding member 60 is in a horizontal state, the user arranges the connection device 1 in the box 80 by moving the connection device 1 downward (side in the arrow Z2 direction) from above (side in the arrow Z1 direction) the box 80. In this case, the user also inserts the reagent extracting tubes 11, 21, 31, 41, and waste fluid discharging tube 51 (tips 11a, 21a, 31a, 41a, 51a) into the corresponding opening 81a, 82a, 83a, 84a, 85a, respectively. Note that the user arranges the connection device 1 in the box 80 while viewing the exposed part A (refer to FIG. 2) and confirming the placement of the reagent extracting tubes 11, 21, 31, 41, and waste fluid discharging tube 51 from above the connection device 1.

Figure 9:
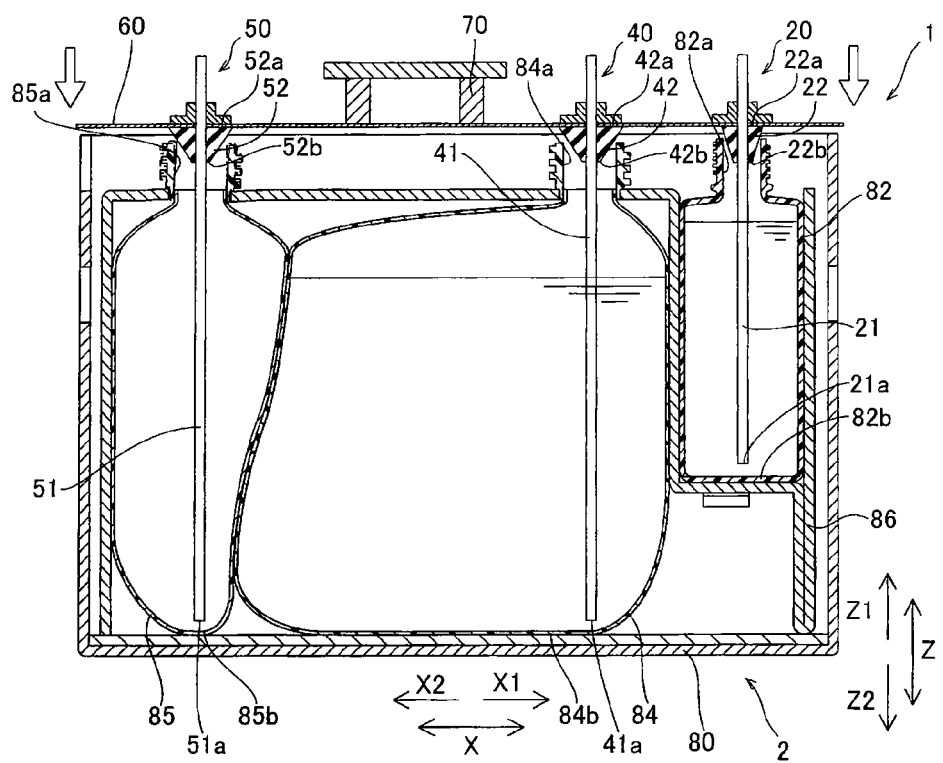
FIG. 9 is a cross sectional view along the 300-300 line of FIG. 2 showing the connection device arrangement and operation in the reagent set in the first embodiment of the present invention; embodiment of the present invention.
Figure 10:
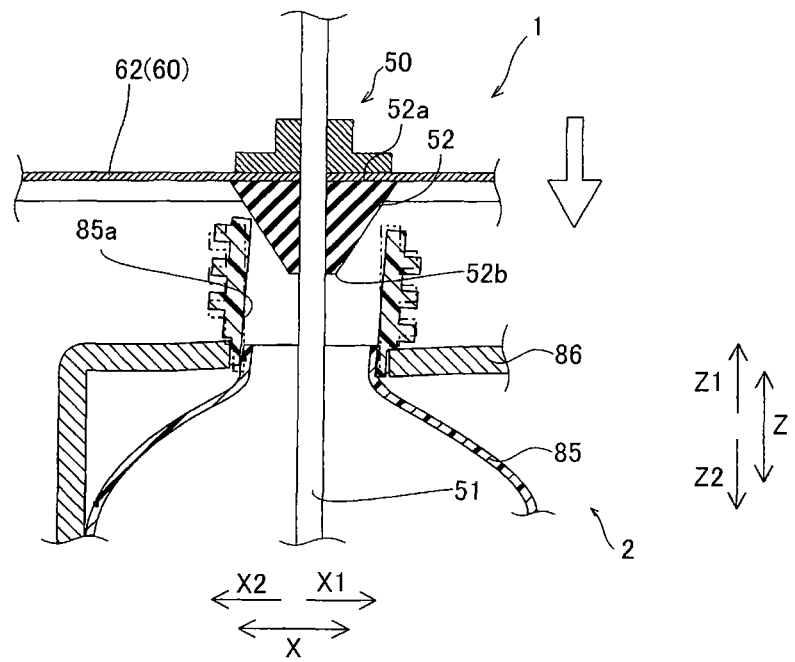
FIG. 10 is an enlarged cross sectional view of the vicinity of the cover member showing the cover member in contact with the opening in the first embodiment of the present invention.
Figure 11:
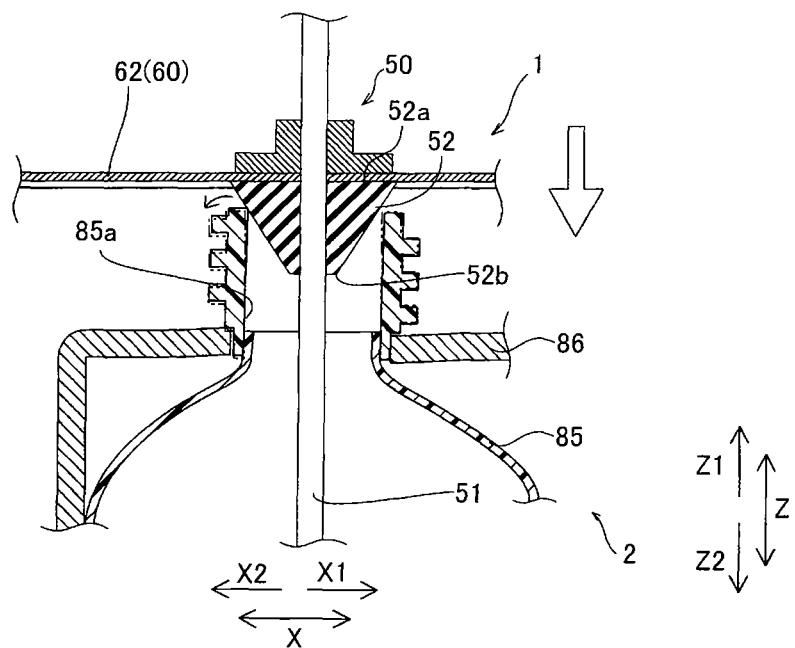
FIG. 11 is an enlarged cross sectional view of the vicinity of the cover member showing the moving opening in the first embodiment of the present invention.

As shown in FIGS. 9 and 10, in the present embodiment, the side surface of the inverted circular cone shaped cover member 52 abuts the inner side surface on the side in the arrow X2 direction of the opening 85a of the waste fluid container 85 when the opening 85a of the waste fluid container 85 dislocates from the predetermined position (double dashed line). In this case, the opening 85a is configured to be movable in a certain range in a horizontal direction. Therefore, when the inclined side surface of the inverted circular cone shaped cover member 52 drops while abutting the top end of the inner side surface of the opening 85a, the opening 85a receives a force from the side surface of the inverted circular cone shaped cover member 52 to move in the horizontal direction so that the center of the opening 85a aligns with the center of the cover member 52. Thus, the opening 85a is automatically adjusted so as to be disposed at a position corresponding to the position of the cover member 52 (waste fluid discharge unit 50) because the opening 85a moves somewhat in the arrow X2 direction along the outer side surface of the cover member 52, as shown in FIG. 11.

Thus, the opening 85a is aligned with a predetermined positional relationship relative to the cover member 52 with the latching parts 61 and 62 disposed on the top end surface of the bilateral side surfaces (side surfaces 80a and 80b) in the Y direction of the box 80, and the cover members 12, 22, 32, 42, and 52 installed on the openings 81a, 82a, 83a, 84a, and 85a, respectively, as shown in FIG. 4. The openings 81a, 82a, 83a, and 84a are also aligned with a predetermined positional relationship with the cover members 12, 22, 32, and 42, respectively, similar to the opening 85a. In this case, the tips 11a, 21a, 31a, 41a, and 51a are positioned near the base (not shown in the drawing) of the hemolytic agent storage container 81, near the base 82b of the hemolytic agent storage container 82, near the base (not shown in the drawing) of the staining agent storage container 83, near the base 84b of the diluting liquid container 84, and near the base 85b of the waste fluid container 85, respectively. Thus, connecting the connection device 1 to the reagent set 2 is completed.

As described in the first embodiment, the cover members 12, 22, and 32 are locked in the openings 81a, 82a, and 83a, respectively, since the top surfaces 12a, 22a, and 32a are not completely fitted in the openings 81a, 82a, and 83a since the surface areas are larger than the openings 81a, 82a, and 83a corresponding to the cover members 12, 22, and 32, because the surface area of the top surfaces 12a, 22a, and 32a of the cover members 12, 22, and 23 are greater than the surface area of the openings 81a, 82a, and 83a. The cover members 12, 22, 32 are installed in the openings 81a, 82a, 83a, respectively, so that part of the cover members 12, 22, 32 block the openings 81a, 82a, 83a, by configuring the cover members 12, 22, 23 so that the cross sectional area continuously decreases from the side in the arrow Z1 direction to the side in the arrow Z2 direction, and the cross sectional shape of the cover members 12, 22, 32 are substantially the same as the shape (circular) of the openings 81a, 82a, 83a of the corresponding cover members 12, 22, 32, respectively. In this way, when the reagent extracting tubes 11, 21, 31, 41, and waste fluid discharging tube 51 are inserted in the hemolytic agent storage container 81, hemolytic agent storage container 82, staining agent storage container 83, diluting liquid container 84, and waste fluid container 85, respectively, the openings 81a, 82a, and 83a, can be individually blocked by the corresponding cover members, 12, 22, and 32, and the openings 84a and 85a can be blocked by a simple structure without providing a precisely designed vertical movement mechanism. The position of the opening 85a can also be adjusted to correspond to the predetermined position of the cover member 52 by moving the opening 85a along the side surface of the cover member 52 by lowering the cover member 52 while the side surface of the cover member 52 abuts the opening 85a via configuring the cover member 52 with a cross sectional area that continuously decreases from the side in the arrow Z1 direction toward the side in the arrow Z2 direction.

As described in the first embodiment, the position of the opening 85a can be more easily adjusted to correspond to the predetermined position of the cover member 52 by configuring the opening 85a to be movable so as to align with the predetermined position of the cover member 51 (waste fluid container 50) of the connection device 1.

As described above in the first embodiment, it is possible to prevent obstructed aspiration of the fluid (diluting liquid) positioned near the base 84b caused by the reagent aspirating tube 41 not being inclined and not inserted to the base 84b by configuring the reagent aspirating tube 41 to prevent such inclination so as to be inserted to the base 84*b* of the diluting liquid container 84 when the connection device 1 is installed.

As described above in the first embodiment, the cover member 52 easily blocks the opening 85*a* even when the waste fluid container 85 has rotated within the horizontal plane relative to the connection device 1 unlike because the cross section plane of the cover member 52 has a circular cross section shape unlike when the cross section plane of the cover member 52 has a polygonal shape.

As described above in the first embodiment, the reagent extracting tubes 11, 21, 31, 41, and waste fluid discharging tube 51 can be easily inserted in the hemolytic agent storage container 81, hemolytic agent storage container 82, staining agent storage container 83, diluting liquid container 84, and waste fluid container 85, respectively, by the user gripping the handle 70 when the handle-shaped handle 70 is mounted to position the connection device 1 in the reagent set 2 while the user holds the holding member 60 substantially in the center in the X direction.

As described above in the first embodiment, the operation when mounting the connection device 1 is improved because the connection device 1 is more easily arranged, while the user verifies whether the reagent extracting tubes 11, 21, 31, 41, and waste fluid discharging tube 51 are inserted in the corresponding openings 81*a*, 82*a*, 83*a*, 84*a*, and 85*a*, respectively, via the exposed part A, by forming the exposed part A on bilateral sides in the Y direction of the latch release 63 to allow verification inside the body 80.

As described above in the first embodiment, the connection device 1 is prevented from dropping into the interior of the box 80 by the latching parts 61 and 62 because the latching parts 61 and 62 are installed on the top end surface of the bilateral side surfaces (side surfaces 80*a* and 80*b*) of the box 80 by having the width W2 of the latching parts 61 and 62 larger than the width W1 in the Y direction of the body 80.

As described above in the first embodiment, the cover members 12, 22, 32, 42, and 52 and the reagent extracting tubes 11, 21, 31, 41, and waste fluid discharging tube 51 are prevented from coming off the hemolytic agent storage container 81, hemolytic agent storage container 82, staining agent storage container 83, diluting liquid container 84, and waste fluid container 85 due to movement of the holding member 60 in the Y direction because movement of the holding member 60 in a horizontal direction (Y direction) can be prevented by the side surfaces 61*a* and 62*a* by providing the side surfaces 61*a* and 62*a*, which regulate the movement of the holding member 60 in the Y direction.

As described above in the first embodiment, the cover members 12, 22, 32, 42, and 52 are inserted in and seal the openings 81*a*, 82*a*, 83*a*, 84*a*, 85*a*, respectively because the cover members 12, 22, 32, 42, and 52 are formed of silicone rubber, compared to cover members made of glass and the like. Thus, the openings 81*a*, 82*a*, 83*a*, 84*a*, and 85*a* are more reliably blocked by the cover members 12, 22, 32, 42, and 52. Corrosion of the cover members 12, 22, 32, 42, and 52 by the reagent and waste fluid is also prevented by forming the cover members 12, 22, 32, 42, and 52 of chemically resistant silicone rubber.

As described above in the first embodiment, the reagent extracting tubes 11, 21, 31, 41 can be inserted into the hemolytic agent storage container 81, hemolytic agent storage container 82, staining agent storage container 83, and diluting liquid container 84 when the cover members 12, 22, 32, 42 are locked in the openings 81*a*, 82*a*, 83*a*, and 84*a* so as to block the openings 81*a*, 82*a*, 83*a*, 84*a* at veterinary hospitals and the like where there are many foreign substances such as animal fur and the like by using the connection device 1 in the sample analyzer 3 which analyzes the blood (samples) of animals. Thus, sample analysis can be performed with greater stability because contamination of the container by foreign substances can be prevented.

(Second Embodiment)

A second embodiment is described below with reference to FIGS. 12 through 20. The second embodiment is described by way of example in which a notch is provided in the cover member of the connection device, a departure from the first embodiment.

The overall structure of the analyzing apparatus 200 of the second embodiment of the present invention is described below with reference to FIGS. 12 through 20.

Figure 12:
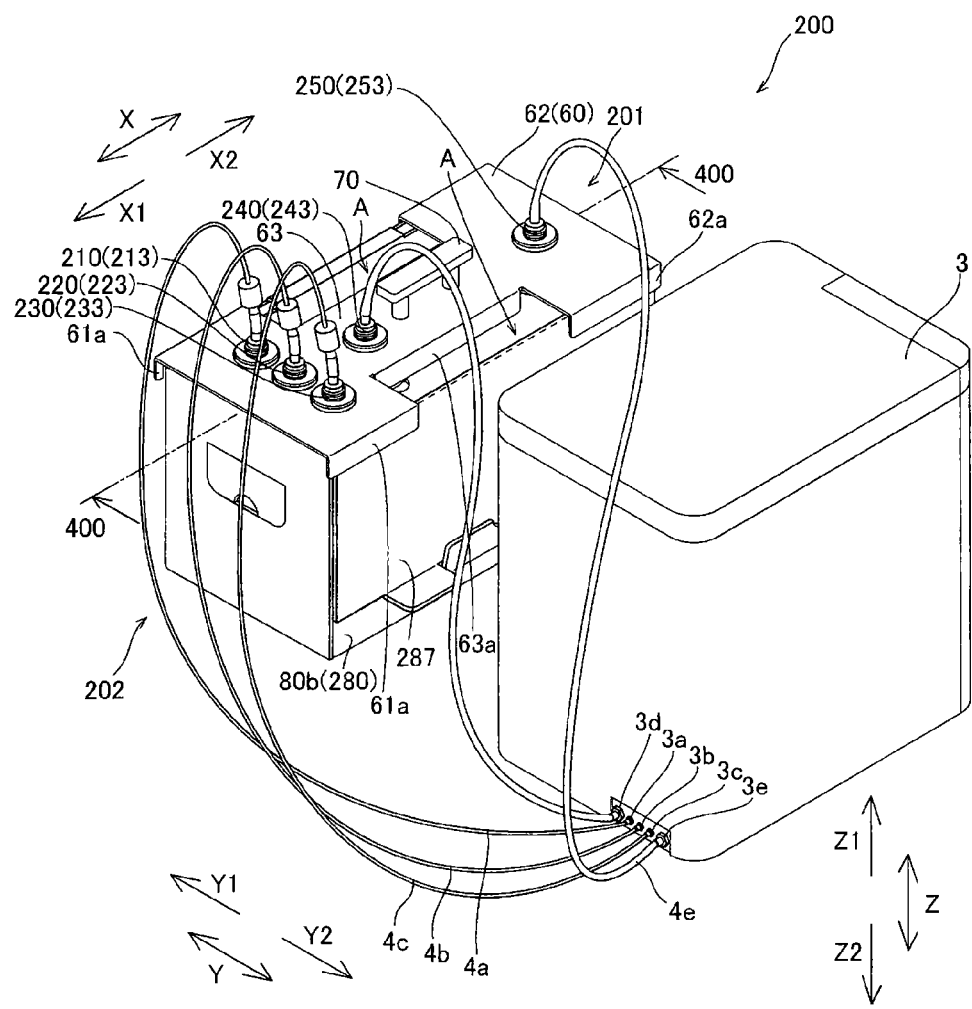
FIG. 12 is a perspective view showing the structure of the connection device, reagent set, and sample analyzer of a second embodiment of the present invention.

As shown in FIG. 12, the analyzing apparatus 200 of the second embodiment is configured by a connection device 201, reagent set 202, and sample analyzer 3.

Figure 13:
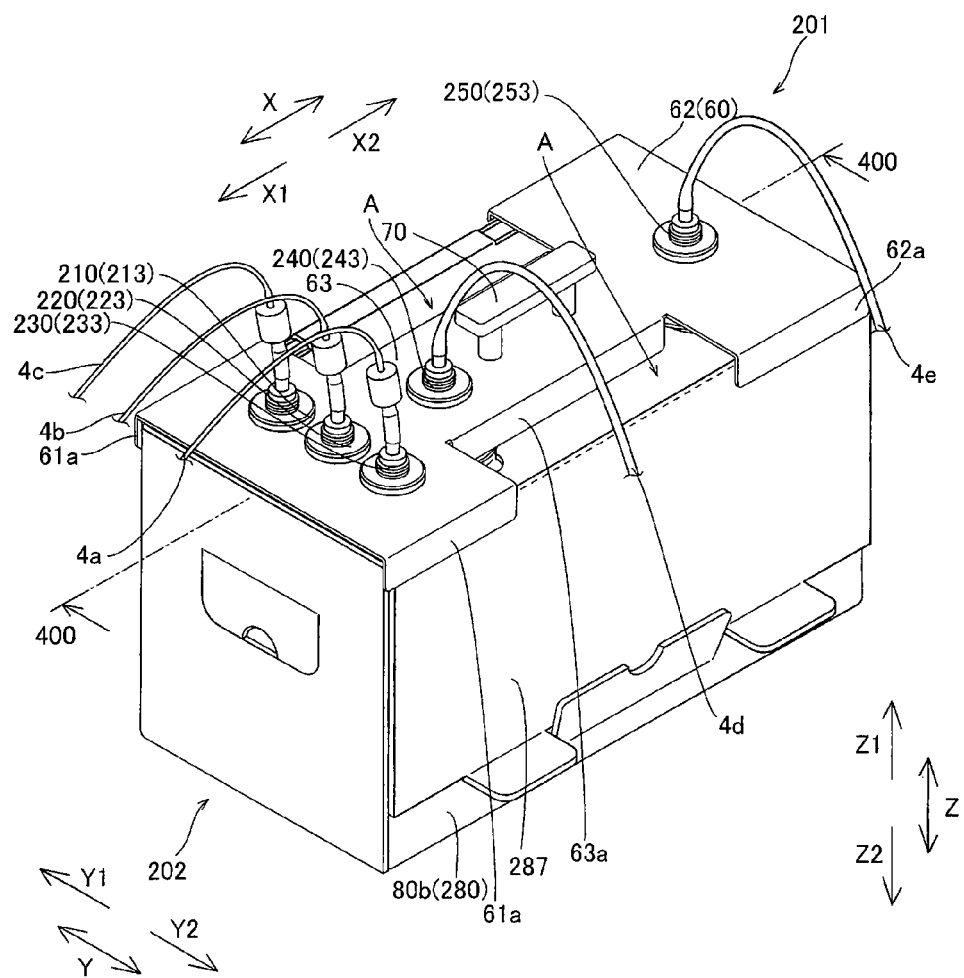
FIG. 13 is a perspective view showing the connection device arranged in the reagent set in the second embodiment of the present invention.
Figure 14:
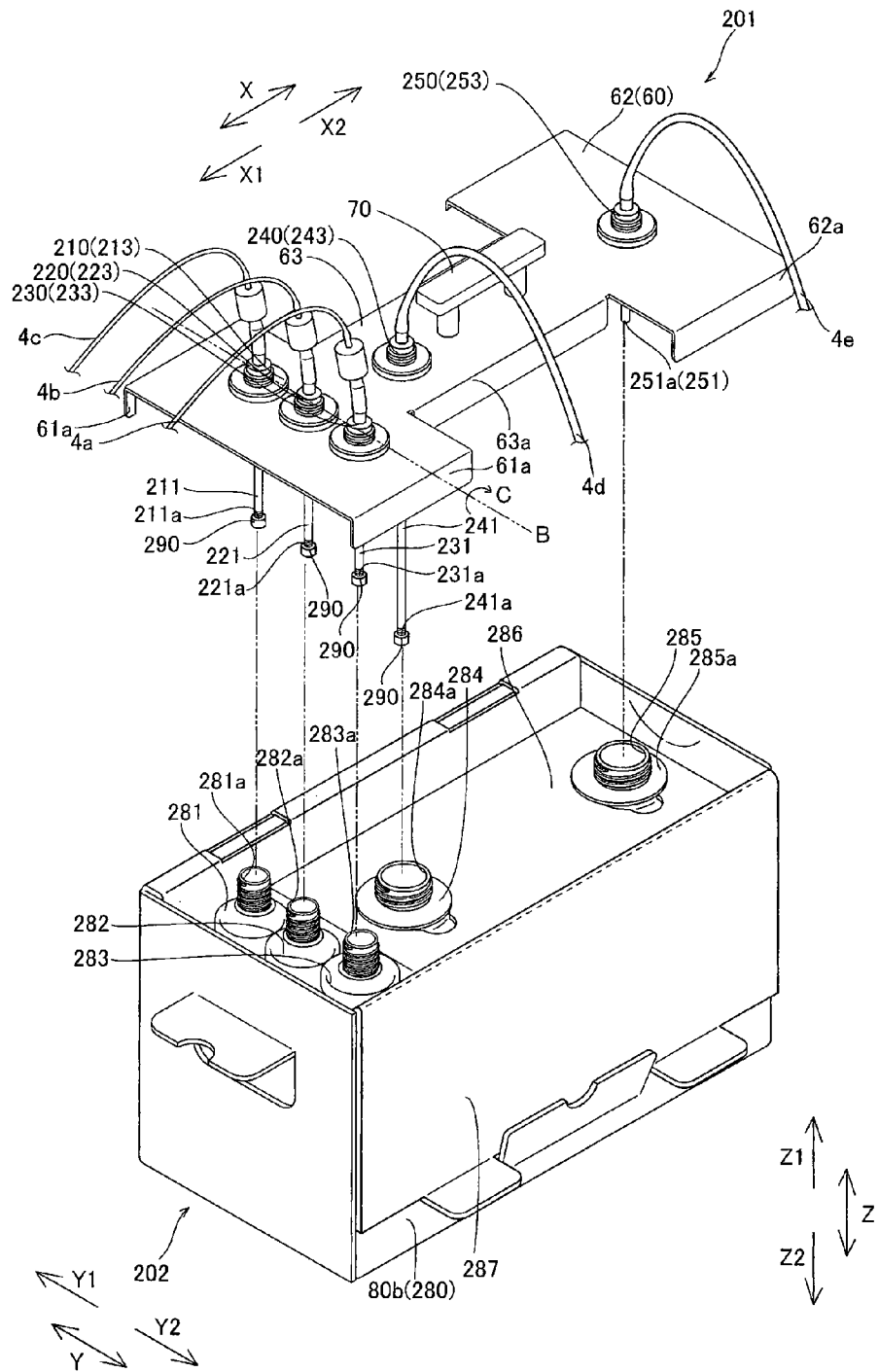
FIG. 14 is a perspective view showing the connection device removed from the reagent set in the second embodiment of the present invention.

As shown in FIGS. 12 through 14, the connection device 201 includes, on the side in the arrow X1 direction, reagent extraction units 210, 220, and 230 disposed in a row in the Y direction, reagent extraction unit 240 disposed near the center in the X direction, and waste fluid discharge unit 250 disposed on the side in the arrow X2 direction. The reagent extraction units 210, 220, 230, 240, and waste fluid discharge unit 250 are anchored and held by a metal holding member 260.

As shown in FIG. 14, in the reagent set 202, a hemolytic agent storage container 281, hemolytic agent storage container 282, staining agent storage container 283, diluting liquid container 284, and waste fluid container 285 are arranged in correspondence with the reagent extraction unit 210, 220, 230, 240, and waste fluid discharge unit 250, respectively, inside a substantially rectangular box 280. An anchor member 286 is arranged inside the box 280 to dispose the hemolytic agent storage container 281, hemolytic agent storage container 282, staining agent storage container 283, diluting liquid container 284, and waste fluid container 285 at predetermined positions. As shown in FIG. 12, the box 280 includes an integrated cover 287 that is mountable so as to cover the top surface thereof.

Figure 15:
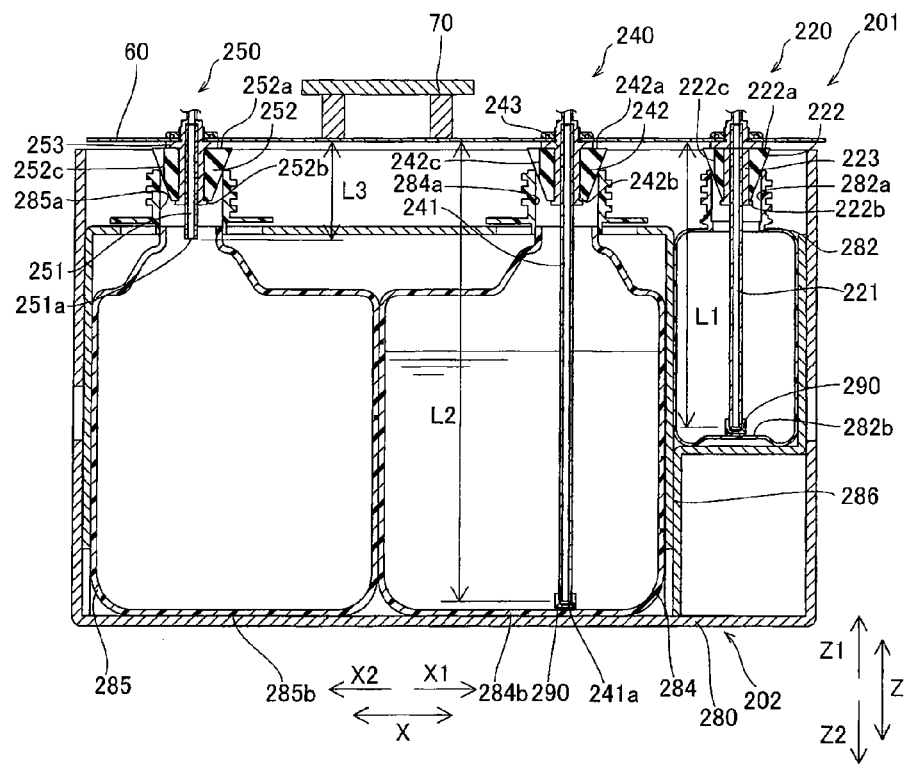
FIG. 15 is a cross sectional view along the 400-400 line of FIG. 13 showing the connection device arranged in the reagent set in the second embodiment of the present invention.

As shown in FIG. 15, the diluting liquid container 284 and waste fluid container 285 are containers of substantially similar shape. The openings 284*a* and 285*a* are movable in a certain range because the diluting liquid container 284 and waste fluid container 285 are configured by a flexible material.

In the second embodiment, as shown in FIG. 15, the reagent extraction units 210, 220, 230, and 240 are provided with connection members 213, 223, 233, 243, respectively, for connecting reagent extracting tubes 211, 221, 231, 241 and cover members 212, 222, 232, 242, respectively. As shown in FIG. 14, the reagent extraction units 210, 220, 230, 240 are provided with filter members 290 that screw onto the tips 211*a*, 221*a*, 231*a*, 241*a* of the reagent extracting tubes 211, 221, 231, and 241. Note that the filter members 290 are easily replaceable by mounting the filter member 290 on the tip 211*a* (221*a*, 231*a*, 241*a*) compared to when the a filter is mounted within the reagent extracting tube 211 (221, 231, 241).

As shown in FIG. 15, the waste fluid discharge unit 250 is provided with a connection member 253 for connecting the waste fluid extracting tube 251 and cover member 252. The waste fluid discharging tube 251 has a length L3 from the holding member 260 to the tip 251*a*. That is, the tip 251*a* of the waste fluid discharging tube 251 is positioned near the opening 285 and is not positioned near the base 285*b* of the waste fluid container 285. Thus, it is possible to prevent bubble formation in the waste fluid when the waste fluid is discharged from the waste fluid discharging tube 251 caused by the positioning of the tip 251a of the waste fluid discharging tube 251 within the waste fluid. Note that the length L3 is less than the lengths L1 (length of the reagent extracting tubes 211, 221, 231) and L2 (length of the reagent extracting tube 241).

Figure 16:
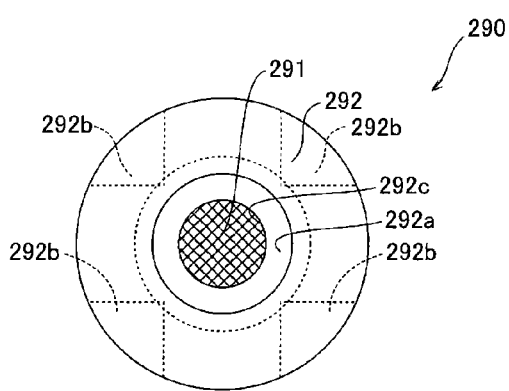
FIG. 16 is a plan view of the filter of the connection device in the second embodiment of the present invention.

As shown in FIG. 16, the filter member 290 includes a filter 291 for removing foreign substances, and an adapter 292 inside which the filter 291 is mountable and which screws onto the tip 211a (221a, 231a, 241a (refer to FIG. 15). The adapter 292 has a threaded part 292a for screwing onto the tip 211a (221a, 231a, 241a), seat 292b, and an inner surface 292c for the placement of the filter 292 and through which the reagent passes. Thus, a foreign substance is removed before passing through the reagent extracting tube 211 (221, 231, 241 (refer to FIG. 15) via the filter 291 mounted on the inner surface 292c.

Figure 17:
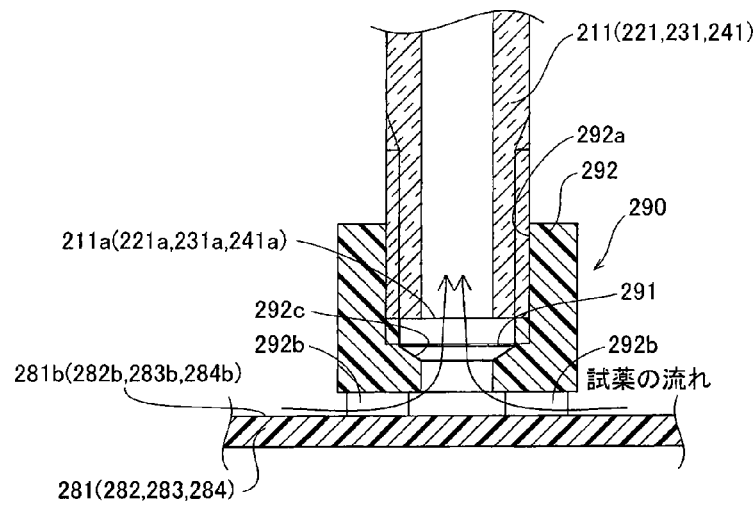
FIG. 17 is an enlarged cross sectional view showing the vicinity of the filter of the connection device in the second embodiment of the present invention.

Four seats 292b are arranged at substantially equal angular (90 degrees) intervals. As shown in FIG. 17, the seat 292b is configured to be in contact with the bottom 281b (bottom 282b of the hemolytic agent storage container 282, bottom 283b of the staining agent storage container 283, bottom 284b of the diluting liquid container 284) of the hemolytic agent storage container 281 when the connecting device 201 is arranged in the reagent set 202. Thus, all the reagent in the hemolytic agent storage container 281 (hemolytic agent storage container 282, staining agent storage container 283, diluting liquid container 284) can be completely aspirated.

Figure 18:
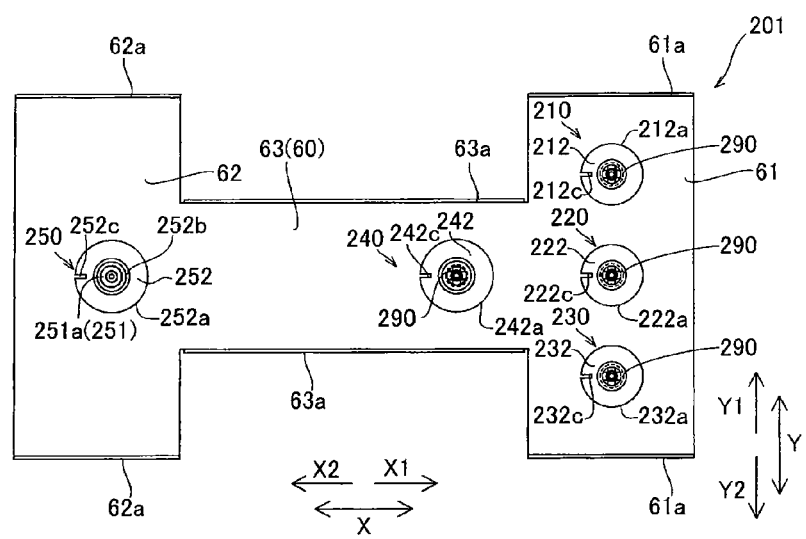
FIG. 18 is a plan view showing the bottom surface side of the connection device in the second embodiment of the present invention.

In the second embodiment, as shown in FIGS. 14 and 15, the cover members 212, 222, 232, 242, and 252 have a circular cross sectional shape in cross section (plane formed by the X direction and Y direction), wherein the cross sectional area (surface area in the plane formed in the X direction and Y direction) continuously decreases from the side in the arrow Z1 direction toward the side in the arrow Z2 direction. As shown in FIG. 18, the side surface of the cover members 212, 222, 232, 242, and 252 are provided with notch 212c, 222c, 232c, 242c, and 252c, respectively, extending downward (arrow Z2 direction in FIG. 15) from the top surface 212a, 222a, 232a, 242a, and 252a.

As shown in FIG. 15, the notches 212c, 222c, 232c, 242c, and 252c are configured to connected the outside with the inside of the hemolytic agent storage container 281 (refer to FIG. 14), hemolytic agent storage container 282, staining agent storage container 283, diluting liquid container 284, and waste fluid container 285, respectively, when the connection device 201 is arranged in the reagent set 202. Specifically, the outside and the inside are respectively connected by positioning the bottom end of the notches 212c, 222c, 232c, 242c, and 252c on the side in the arrow Z2 direction from the top end of the opening 281a of the hemolytic agent storage container 281 (refer to FIG. 14), opening 282a of the hemolytic agent storage container 282, opening 283a of the staining agent storage container 283 (refer to FIG. 14), opening 284a of the diluting liquid container 284, and opening 285a of the waste fluid container 285.

Figure 19:
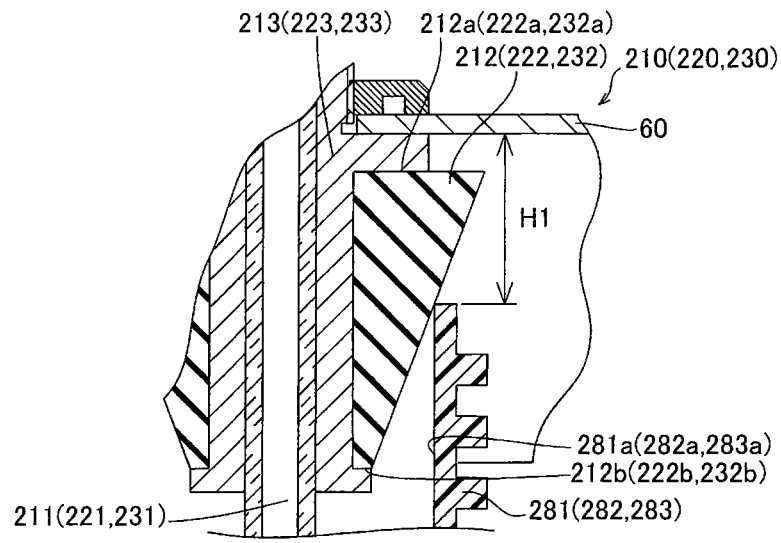
FIG. 19 is an enlarged cross sectional view showing the vicinity of the cover members corresponding to the hemolytic agent storage container and staining agent storage container in the second embodiment of the present invention.
Figure 20:
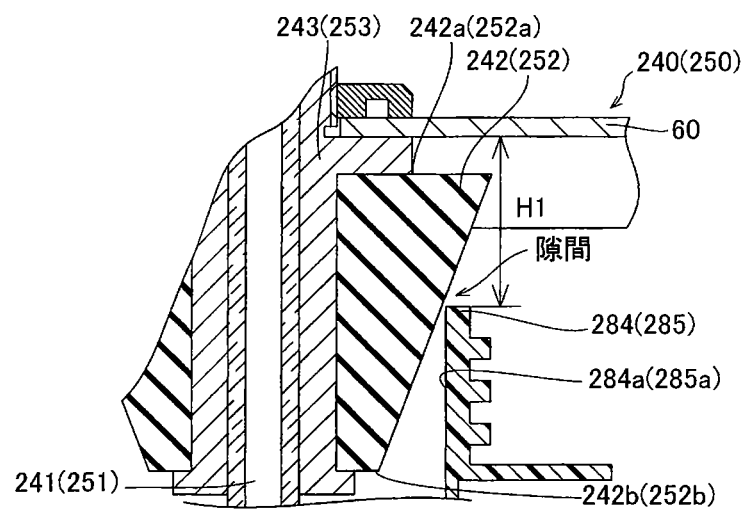
FIG. 20 is an enlarged cross sectional view showing the vicinity of the cover members corresponding to the diluting liquid container and waste fluid container in the second embodiment of the present invention.

In the second embodiment, as shown in FIG. 19, the cover members 212, 222, 232, and openings 281a, 282a, 283a are configured to make contact with the top end of the openings 281a, 282a, 283a separated from the holding member 260 by a distance H1 when the connection device 201 is arranged in the reagent set 202 by moving the holding member 60 in a substantially horizontal state downward from above. As shown in FIG. 20, however, with the top end of the openings 284a and 285a separated a distance H1 from the holding member 60, the cover members 242 and 252 are not in contact with the openings 284a and 285a inasmuch as a gap is formed between the openings 284a and 285a and the cover members 242 and 252. That is, the cover members 212, 222, 232 and the openings 281a, 282a, 283a make contact before the cover members 242, 252, and openings 284a and 285a.

Therefore, as shown in FIG. 14, an axis B is set at standard in a lateral direction passing through the opening 281a, 282a, and 283a disposed in a row in the Y direction (lateral direction) near the end of the box 80 on the side in the arrow X1 direction, and the connection device 201 is movable in rotation direction C by pivoting on the axis B. Thus, the reagent extracting tube 241 and waste fluid discharging tube 251 are sequentially inserted in the openings 284a and 285a, respectively, which are disposed in a row in the X direction (longitudinal direction) substantially in the center in the X direction of the box 280.

Note that the structure of the second embodiment is in other aspects identical to that of the first embodiment.

The arrangement and operation of the connection device 201 in the reagent set 202 of the second embodiment of the present invention is described below with reference to FIG. 14.

In the second embodiment, as shown in FIG. 14, when the user arranges the connection device 201 in the box 280 while moving the connection device 201 downward (side in the arrow Z2 direction) from above the (side in the arrow Z1 direction) the box 280 (reagent set 202), the contact between the openings 281a, 282a, 283a and the cover members 212, 222, 232 positioned near the end of the box 280 on the side in the arrow X1 direction occurs before the contact between the openings 284a, 285a and the cover members 284a and 285a positioned substantially in the center of the box 280 in the X direction. Thereafter, the cover member 242 and opening 24a make first contact, then the cover member 252 and opening 285a make contact by slightly rotating the connection device 201 in rotation direction C by pivoting on the axis B. As a result, the reagent extracting tubes 211, 221, 231, 241, and waste fluid discharging tube 251 are inserted into the hemolytic agent storage container 281, hemolytic agent storage container 282, staining agent storage container 283, diluting fluid container 284, and waste fluid container 285, respectively.

Note that the arrangement and operation of the second embodiment are in other aspects identical to that of the first embodiment.

As described above in the second embodiment, substantially the same air pressure is maintained inside and outside the hemolytic agent storage container 281, hemolytic agent storage container 282, staining agent storage container 283, diluting fluid container 284, and waste fluid container 285 even when the openings 281a, 282a, 283a, 284a, and 285a are blocked by the cover members 212, 222, 232, 242, 252, respectively, by providing the notches 212c, 222c, 232c, 242c, and 252c in the side surface of the cover members 212, 222, 232, 242, and 252. Thus, it is possible to prevent difficulty when aspirating reagent through the reagent extracting tubes 211, 221, 231, and 241 caused by the sealed hemolytic agent storage container 281, hemolytic agent storage container 282, staining agent storage container 283, and diluting liquid container 284. It is possible to connect the inside and the outside of the hemolytic agent storage container 281, hemolytic agent storage container 282, staining agent storage container 283, diluting liquid container 284, and waste fluid container 285 via a simple structure by providing the notches 212c, 222c, 232c, 242c, and 252c.

As described above, the second embodiment provides the filter 291, which is capable of removing a foreign substance before it passes through the reagent extracting tube 211, 221, 231, and 241; therefore, the filter 291 prevents the foreign substance from reaching the sample analyzer 3 even when a foreign substance has contaminated the hemolytic agent storage container 281, hemolytic agent storage container 282, staining agent storage container 283, and diluting liquid container 284 via the openings 281a, 282a, 283a, 284a when the covers 212, 222, 232, 242 are mounted.

As described above, the second embodiment is configured so that the openings 281a, 282a, 283a and cover members 212, 222, 232 positioned near the end of the box 280 on the side in the arrow X1 direction come into contact before the openings 284a and 285a come into contact with cover members 242 and 252 positioned substantially in the center of the box 280 in the X direction; the positional alignment of the cover members 212, 222, 232 relative to the hemolytic agent storage container 281, hemolytic agent storage container 282, and staining agent storage container 283 occurs first along the Y direction (lateral direction) near the end of the box 280 on the side in the X1 direction; with axis B as a standard, the reagent extracting tube 241 and waste fluid discharging tube 251, which correspond to the diluting liquid container 284 and waste fluid container 285 aligned in the X direction (longitudinal direction) substantially in the center of the box 280 in the X direction, are sequentially inserted into the diluting liquid container 284 and waste fluid container 285, respectively. Thus, it becomes difficult for inclination of the connection device 201 to occur in the rotation direction pivoting on the axis in the X direction (longitudinal direction). As a result, the reagent extracting tubes 211, 221, 231, 241 and waste fluid discharging tube 251 can be easily inserted in the respective containers by preventing positional dislocation of the mounting position of the connection device 201 caused by inclination of the connection device 201.

Note that the embodiments of the present disclosure are in all respects examples and are not to be considered as limiting in any way. The scope of the present invention is defined solely by the appended claims, is not affected to any degree by the statements within this summary, and includes all modifications which fall within the meanings and equivalences of the scope of the claims.

For example, although the first and second embodiments are described by way of examples in which the reagent extraction units 10, 20, 30, 40 and waste fluid discharge unit 50 (reagent extraction units 210, 220, 230, 240, and waste fluid discharge unit 250) are provided in the connection device 1 (201), the present invention is not limited to these examples. The reagent extraction unit and waste fluid discharge unit of the present invention may be provided in numbers of two or more, less than four, or more than six. Moreover, either the reagent extraction unit or waste fluid discharge unit may be provided in plurality.

Although the first and second embodiments are described by way of examples in which the cover members 12, 22, 32, 42, and 52 (212, 222, 232, 242, 252) have a circular cross sectional shape in the cross sectional plane, the present invention is not limited to these examples. The cover member of the present invention may have a shape other than circular insofar as the shape is substantially similar to the shape of the opening of the fluid container. For example, the shape may be ovoid, or polygonal, such as triangular.

Figure 21:
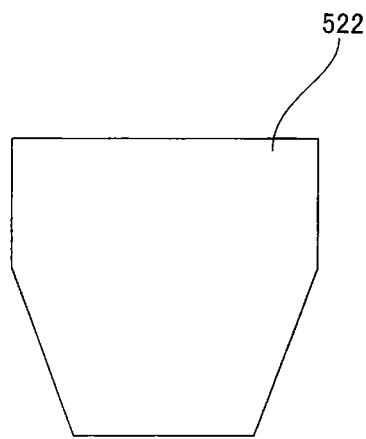
FIG. 21 is a side view showing a modification of the cover members in the first and second embodiments of the present invention.

Although the first and second embodiments are described by way of examples in which the cross sectional surface area of the cover members 12, 22, 32, 42, and 52 (212, 222, 232, 242, 252) is continuously decreasing from the top surface 112a, 22a, 32a, 42a, 52a (212a, 222a, 232a, 242a, 252a) to the bottom surface 12b, 22b, 32b, 42b, 52b (212b, 222b, 232b, 242b, 252b), the present invention is not limited to these examples. The cover member of the present invention, for example, may have a cross sectional surface area that continuously decreases from near the middle, without varying the cross sectional surface area at the top part insofar as the cross sectional surface area continuously decreases in a region that comes into contact with the opening of the corresponding container, as in the modification of the cover member of the first and second embodiment shown in FIG. 21.

Although the second embodiment is described by way of example in which notches 212c, 222c, 232c, 242c, 252c are formed in the cover members 212, 222, 232, 242, 252, respectively, the present invention is not limited to this example. The connection between the inside and outside of the fluid container in the present invention is not limited to a notch. For example, a hole passing through the cover member also may be provided.

Although the first and second embodiments are described by way of examples in which the holding member 60 has the shape of the letter H in a planar view, the present invention is not limited to this example. For example, the holding member may have a shape other than the letter H insofar as part of the box is exposed in a planar view.

Although the second embodiment is described by way of example in which a filter member 290, which incorporates a filter 291, is screwed onto the tip 211a, 221a, 231a, 241a of the reagent extracting tubes 211, 221, 231, 241, respectively, the present invention is not limited to this example. The filter also may be fitted to the inner side surface of the reagent extracting tube.

Although the second embodiment is described by way of example in which the openings 281a, 282a, 283a are aligned in a row in the Y direction (lateral direction) near the end of the box 280 on the side in the arrow X1 direction, and the openings 284a and 285a are aligned in a row in the X direction (longitudinal direction) substantially in the center in the X direction of the box 280, the present invention is not limited to this example. In the present invention, the plurality of openings also may be disposed in the lateral direction substantially in the center of the box, or the plurality of openings also may be disposed in the longitudinal direction near the end of the box.

Although the first and second embodiments are described by way of examples in which an elevator mechanism is not provided to vertically move the connection device 1 (201) in a predetermined path, the present invention is not limited to this example. In the present invention, an elevator mechanism also may be provided to move the vertically move the connection device in a predetermined path. In this case, the elevator mechanism need not be precision designed since the position of the opening of each container can be finely adjusted by the cover member.

What is claimed is:

1. A combination of reagent set and a connection device for providing fluid paths between a plurality of fluid containers in the reagent set and a sample analyzer body for analyzing samples using reagent, comprising:
   a reagent box in which the plurality of fluid containers are stored so as to maintain openings of the fluid containers generally in a predetermined geometry in a first plane, the reagent box comprising a peripheral side wall that surround all sides of the stored fluid containers so as to keep the fluid containers inside the reagent box;
   a plurality of tubular members each being inserted in the respective fluid container through the opening thereof;
   a generally planar holding member placed on the reagent box to cover the reagent box and comprising a pair of latching parts formed, respectively, at a pair of first sides of the holding member, the first sides of the holding member running in a first direction, the pair of latching parts being engaged with upper end portions of the reagent box to position the holding member relative to the reagent box, the holding member further comprising a pair of exposed parts formed, respectively, at the first sides of the holding member, the pair of exposed parts being arranged in a second direction perpendicular to the first direction and being shaped to configure the holding member in a form of letter "H" in its plan view and sized sufficiently large to make inside of the reagent box visible from outside thereof through the exposed parts; and a plurality of cover members fixed in the predetermined geometry to the holding member and each fitted in the opening of the respective fluid container in the reagent box, wherein the plurality of cover members are each shaped to have concentric circular peripheries arranged parallel to the first plane and narrower towards an end of the cover member located inside the fluid containers, and the openings of the fluid containers are substantially immobilized with respect to the holding member solely by engagement with the circular peripheries of the cover members.

2. The combination of claim 1, wherein the openings of the fluid containers are immobilized in the predetermined geometry through contact with the concentric peripheries of the cover members when the cover members are mounted.

3. The combination of claim 1, wherein the cover members are generally conical.

4. The combination of claim 1, wherein the cover members each comprises a notch for communicating the inside of the fluid container with the outside thereof.

5. The combination of claim 4, wherein the notch runs across the concentric peripheries of the cover member.

6. The combination of claim 1, wherein at least one of the plurality of fluid containers is a reagent container.

7. The combination of claim 6, further comprising a filter for preventing foreign material from passing through the tubular member inserted in the reagent container.

8. The combination of claim 7, wherein the filter is disposed at an end of the tubular member inserted in the reagent container.

9. The combination of claim 1, wherein the holding member comprises a handle to be grasped by a user.

10. The combination of claim 1, wherein the holding member is shaped such that at least one tubular member is visible from above the holding member.

11. The combination of claim 1, wherein the latching part is of a width wider than a width of the reagent box at locations where the latching part is engaged with the reagent box.

12. The combination of claim 1, wherein the cover member is formed of rubber.

13. The combination of claim 1, wherein
the reagent box is in a substantially rectangular shape having lateral ends and longitudinal ends in a plane view;
the plurality of fluid containers comprise a plurality of first fluid containers with openings arranged in a row in a lateral direction of the reagent box near a first longitudinal end of the reagent box, and a plurality of second fluid containers with openings arranged in a row in a longitudinal direction of the reagent box around a center of the reagent box;
the cover members comprise first cover members fitted in the openings of the first fluid containers, and second cover members fitted in the openings of the second fluid containers; and
the first and second cover members are configured such that the holding member is rotated slightly down from the first longitudinal end towards the second longitudinal end, resulting from that when the holding member is lowered towards the reagent box, the openings of the first fluid containers come into contact with the first cover members before the openings of the second fluid containers come into contact with the second cover members, and the holding member rotates down towards the second longitudinal end of the reagent box after the openings of the first fluid containers come into contact with the first cover members and before the openings of the second fluid containers come into contact with the second cover members.

14. An analyzer comprising:
the combination of claim 1; and
an analyzer body configured to analyze samples using fluids supplied from the fluid containers via the connection device.

15. The analyzer of claim 14, wherein the analyzer body is configured to analyze a sample from an animal.

* * * * *